United States Patent [19]
Albaugh et al.

[11] Patent Number: 5,453,434
[45] Date of Patent: Sep. 26, 1995

[54] N-SUBSTITUTED DERIVATIVES OF 3R,4R-ETHYL-[(1-METHYL-1H-IMIDAZOL-5-YL)METHYL]-2-PYRROLIDONE

[75] Inventors: Pamela Albaugh, Clinton, Conn.; Gregory J. White, Alpharetta, Ga.; Michael E. Garst, Newport Beach, Calif.

[73] Assignee: Allergan, Inc., Irvine, Calif.

[21] Appl. No.: 265,163

[22] Filed: Jun. 24, 1994

Related U.S. Application Data

[60] Continuation-in-part of Ser. No. 126,285, Sep. 20, 1993, which is a division of Ser. No. 434,929, Nov. 13, 1989, Pat. No. 5,264,449.

[51] Int. Cl.$^6$ .................. A61K 31/415; C07D 405/14
[52] U.S. Cl. ............................. 514/397; 548/314.7
[58] Field of Search .................. 514/397, 912; 548/314.7

[56] References Cited

U.S. PATENT DOCUMENTS

| | | | |
|---|---|---|---|
| 3,470,197 | 9/1969 | VanDyke | 514/397 |
| 5,264,449 | 11/1993 | Albaugh | 514/397 |

OTHER PUBLICATIONS

Noller, Textbook of Organic Chemistry, 2nd Ed., W. B. Saunders Co., Philadelphia, p. 185, (1962).

*Primary Examiner*—Jacqueline Haley
*Attorney, Agent, or Firm*—Robert J. Baran; Martin A. Voet; James Mark Hoch

[57] ABSTRACT

The present invention relates to new carbonyl 3R, 4R-ethyl-[(1-methyl-1H-imidzaol-5-yl)methyl]-2-pyrrolidinone derivatives carrying a carboxyester-type lipophilic moiety on the pyrrolidinone nitrogen and are valuable antiglaucoma agents and targeted for use in the treatment of so-called dry eye.

More particularly, the present invention concerns new N-substituted carbonyl-3R, 4R-ethyl-[(1-methyl-1H-imidazol-5-7)methyl]-2-pyrrolidinone derivatives of the formula (I):

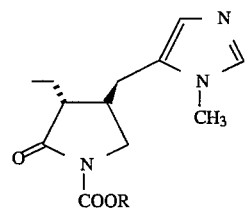

wherein R is selected from the group consisting of

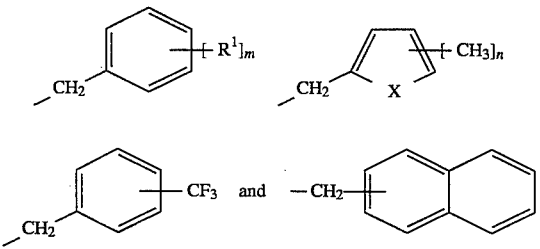

wherein $R^1$ is a halo radical, e.g. a chloro radical, or a lower alkyl radical, e.g. a methyl or ethyl radical, with the proviso that when m is 1, $R^1$ is not methyl or t-butyl, m is an integer of 1 or 2, n is 0 or an integer of 1 or 2 and X is O or S, and pharmaceutically-acceptable acid addition salts thereof.

5 Claims, No Drawings

N-SUBSTITUTED DERIVATIVES OF 3R,4R-ETHYL-[(1-METHYL-1H-IMIDAZOL-5-YL)METHYL]-2-PYRROLIDONE

CROSS REFERENCE TO RELATED APPLICATIONS

This patent application is a continuation in part of U.S. patent application Ser. No. 08/126,285, which was filed on Sep. 20, 1993 in the name of Albaugh, which is a divisional of U.S. patent application Ser. No. 07/434,929, which was filed on Nov. 13, 1989, in the name of Albaugh and is now U.S. Pat. No. 5,264,449.

BACKGROUND OF THE INVENTION

1. Field of Invention

The present invention relates to new chemical compounds having valuable pharmacological properties. More particularly, the present invention concerns novel, pharmaceutically active N-substituted derivatives of 3R, 4R-ethyl-[(1-methyl-1H-imidazol-5 -yl)methyl}-2-pyrrolidinone.

2. Description of Related Art

The compound, used in the preparation of the compounds of the present invention, 3R, 4R-ethyl[(1-methyl-1H-imidazol-5-yl)methyl]-2 -pyrrolidinone, is known in the art and, together with other 1-alkyl substituted derivatives of the same basic structure, is disclosed in the U.S. Pat. No. 3,470,197. There, it and certain derivatives are described as useful antiglaucoma agents. Koda, et al., J. Pharm. Sciences, 62, 2021 (1973) describes certain of the compounds of U.S. Pat. No. 3,470,197 as possessing cholinergic activity.

Structurally, the parent compound is related to the corresponding lactone, from which it can be prepared. The lactone is a known antiglaucoma agent: 3S, 4R-3-ethyl-4-[(1-methyl-1H-imidazol-5 -yl)methyl]-3,4-dihydro-2(3H)-furanone, i.e. pilocarpine. Both compounds lower intraocular pressure via contraction of the ciliary muscle, and also cause simultaneous contraction of the iris muscle leading to decrease in pupil diameter (miosis) in the patient's eye following topical administration. Pilocarpine is an optically active (3S, 4R) compound that is stereoisomeric with isopilocarpine, the optically active trans-isomer (3R,4R). Although pilocarpine is one of the commonly used outflow enhancing drugs used for glaucoma therapy, its use is limited because of its short duration. The major objective of the present invention has been to develop pilocarpine analogues with increased duration of action and improved corneal penetration over pilocarpine.

SUMMARY OF THE INVENTION

The present invention relates to new carbonyl 3R, 4R-ethyl-[(1 -methyl-1H-imidazol-5-yl)methyl]-2-pyrrolidinone derivatives carrying a carboxyester-type lipophilic moiety on the pyrrolidinone nitrogen. More particularly, the present invention concerns new N-substituted carbonyl-3R, 4R-ethyl-[(1-methyl-1H-imidazol-5-yl)methyl]-2 -pyrrolidinone derivatives of the formula (I):

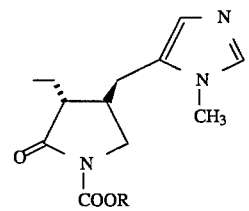

wherein R is selected from the group consisting of

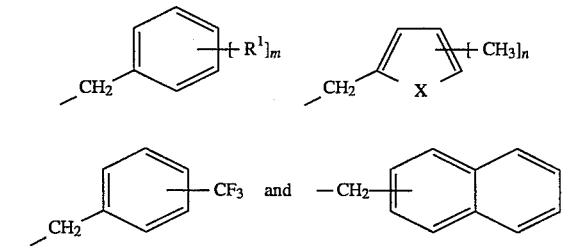

wherein $R^1$ is a halo radical, e.g. a chloro radical or a lower alkyl radical, e.g. a $C_1$ to $C_4$ alkyl radical, with the proviso that when m is 1, $R^1$ is not 4-methyl or t-butyl, m is an integer of 1 or 2, n is 0 or an integer of 1 or 2 and X is O or S, and pharmaceutically-acceptable acid addition salts thereof. Preferably, $R^1$ is chloro, methyl or ethyl.

In another aspect, the present invention relates to a process for the preparation of a racemic or optically active compound defined in Formula (I), which comprises reacting a racemic or optically active compound formula (II)

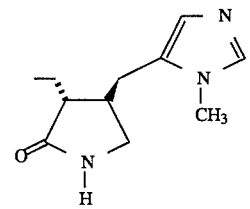

or an acid addition salt thereof, with an N-acylating agent capable of replacing hydrogen attached to the pyrrolidinone nitrogen in the compounds of formula (II) with a —$CO_2R$ group. If desired, the obtained compounds can be converted into their pharmaceutically acceptable salts, or freed from the obtained acid addition salts. If a racemic starting compound is employed, compounds of the formula (I) are obtained as racemates that can be resolved into the respective enantiomers by methods known in the art. [Jacques, J.; Collet, A.; Wileu, S. H. "Enantiomers, Racemates and Resolutions"; Wiley, N.Y. 1981.]

The new compounds of the formula (I) are potent ocular hypotensives that are valuable antiglaucoma agents. They are also targeted for use in the treatment of so-called dry eye, and demonstrate greater topical activity over the parent compound. Accordingly, in a further aspect, the present invention relates to pharmaceutical compositions containing these compounds of their pharmaceutically acceptable salts, as active ingredients.

DETAILED DESCRIPTION OF THE INVENTION

The starting compound is the synthesis of the compounds of formula (I) (R is as hereinabove defined) is 3R, 4R-ethyl-[(1-methyl-1 H-imidazol-5-yl)methyl]-2-pyrrolidinone [formula (II)], that can be prepared by reaction of pilocarpine with ammonia in a suitable solvent inert under the reaction conditions, as described in the U.S. Pat. No. 3,470,197. The preferred solvent is ammonia itself. The reaction is a single step reaction and is conveniently performed in an autoclave or high pressure reactor.

According to the invention, a racemic or optically active compound of formula (II) or an acid addition salt thereof, is N-acylated to obtain the desired N-substituted derivatives hereof of the formula (I).

Preferably, a compound of the formula (II) is reacted with a halo-or cyanoformate derivative of the formula (III):

YCO₂R (III)

or with an anhydride of the formula (IV):

R²O₂COCO₂R (IV)

wherein R is as hereinabove defined,
Y is halogen or a cyano group, and R² is an optionally substituted hydrocarbon group that is identical with or different from R, both in the presence of a base.

Alternatively, the acylation of the compounds of formula (II) may be performed with suitable active esters or carbonates, such as the o-p-nitrophenyl carbonates of the formula (V):

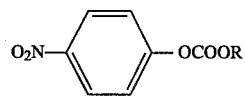

wherein R is as hereinable defined.

Particularly preferred compounds of formula (I) are, for example:

(3R,4R )-1-carbo-(1-naphthylmethyloxy)-3-ethyl-4 -[(1-methyl-1H-imidazol-5-yl)methyl]-2-pyrrolidinone (3R,4R )-1-carbo-(4-trifluoromethylbenzoxy)-3-ethyl-4-[(1-methyl-1H-imidazol-5-yl)methyl]-2-pyrrolidinone (3R,4R)-1-carbo-(2-methylthienyl methyloxy)-3-ethyl-4-[(1 -methyl-1H-imidazol-5-yl)methyl]-2-pyrrolidinone.

(3R, 4R)-1-carbo-(2,4-dimethylbenzoxy)3-ethyl-4-[(1-methyl-1 H-imidazol-5-yl)methyl]-2-pyrrolidinone (3R, 4R )-1-carbo-(3-methylbenzoxy)3-ethyl-4-[(1 -methyl-1H-imidazol-5-yl)methyl]-2-pyrrolidinone (3R, 4R)-1-carbo-(2,3-dimethylbenzoxy)3-ethyl-4-[(1-methyl-1H-imidazol-5-yl)methyl]-2-pyrrolidinone (3R, 4R)-1-carbo-(2-methylbenzoxy)3-ethyl-4-[(1-methyl-1 H-imidazol-5-yl)methyl]-2-pyrrolidinone (3R, 4R)-1-carbo-(4-chlorobenzoxy)3-ethyl-4-[(1-methyl-1 H-imidazol-5-yl)methyl]-2-pyrrolidinone (3R, 4R)-1-carbo-(4-ethylbenzoxy)3-ethyl-4-[(1-methyl-1 H-imidazol-5-yl)methyl]-2-pyrrolidinone If desired, an obtained compound of formula (I), wherein R has the same meanings as defined above, is converted into a pharmaceutically acceptable acid addition salt thereof, or an obtained acid addition salt is converted into the respective free compound or into another pharmaceutically acceptable acid addition salt.

Acid addition salts may be formed with suitable mineral or organic acids, such as hydrochloric acid, hydrobromic acid, sulfuric acid, citric acid, oxalic acid, lactic acid, maleic acid, etc., and can be prepared by methods known per se. The foreseeable requirement is that they be pharmaceutically acceptable for administration to man.

Methods for resolution of racemic compounds of the formula (I) are known in the art, and are disclosed in ordinary textbooks of organic chemistry, such as in Jacques, J; Collet, A.; Wileu, S. H., supra.

The reaction of the starting compound of formula (II) with the halo- or cyanoformates of the formula (III) or the anhydrides of formula (IV) is performed in a suitable solvent, preferably inert under the reaction conditions. Suitable solvents include, but are not limited to tetrahydrofuran and dimethylformamide.

The reaction is performed in the presence of a strong base, such as potassium hydride, sodium hydride, lithiodiisopropylamide (that may be prepared by the reaction of diisopropylamine and n-butyl lithium).

Although the reaction temperature is not critical, the reaction is preferably performed at a temperature between about −100° C. and about 50° C., more preferably at about −78° C. or 0° C., depending on the reactants and solvents employed.

Similarly, the acylation with the O-p-nitrophenyl carbonates of the formula (V) is performed in an inert solvent, preferably in the presence of a strong base, such as potassium or sodium hydride, preferably between ambient temperature and 0° C.

The new compounds of the present invention exhibit valuable pharmacological properties. More particularly, these compounds lower intraocular pressure in the eye, and have increased topical activity over the previously described pharmaceutically active, starting compound.

Pharmaceutical compositions may be prepared by combining a therapeutically efficient amount of at least one compound of the formula (I), wherein R is a hereinabove defined, or a pharmaceutically acceptable salt thereof, as an active ingredient, with conventional pharmaceutical excipient. For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives and stabilizers.

Preferred preservatives that may be used in the pharmaceutical compositions of the present invention include, but are not limited to, benzalkonium chloride, chlorobutanol, thimerosal, phenylmercuric acetate and phenylmercuric nitrate.

Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. The include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agents is edetate disodium, although other chelating agents may also be used in place or in conjunction with it.

The ingredients are usually used in the following amounts:

| Ingredient | Amount (% w/v) |
|---|---|
| Muscarinic Agonist | 0.1–5 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| Antioxidant | as needed |
| Purified Water | as needed to make 100% |

Further details of the invention are illustrated by the following, examples which are not intended to limit the scope of the appended claims.

EXAMPLE 1

(3R, 4R)-1-carbo-(4-ethylbenzoxy)-3-methyl-4[(1-methyl-1H-imidazol-5-yl)methyl]-2-pyrrolidinone To a mixture of potassium hydride (26 mg, 0.65 mmol) and methanol (1.6 mg, 0.05 mmol) in tetrahydrofuran (THF) (4 mL) at 0° was added (3R, 4R)-3-ethyl-4[(1-methyl-1H-imidazol-5-yl)methyl]-2-pyrrolidinone (98 mg, 0.47 mmol) in THF (1.5 mL) via cannula, followed by a THF (0.5 mL) rinse. The reaction mixture was allowed to stir at 0° for 10 minutes, then ambient temperature for 1.5 hours. The reaction mixture was then cooled at 0° C., and O-(4-nitrophenyl)-O'-4-ethylbenzyl) carbonate (181 mg, 0.63 mmol) in THF (1.5 mL) was added via cannula, followed by a THF (0.5 mL) rinse. The reaction mixture was allowed to stir at 0° C. for 10 minutes, then ambient temperature for 18 hours. The reaction was quenched with saturated sodium bicarbonate. The solution was then extracted three times (3X) with methylene chloride, the combined organic layers were dried (over $Na_2SO_4$), filtered, concentrated and the residue was chromatographed on silica gel (3.5% MeOH saturated with $NH_3/CHCl_3$) to give 71.7 mg of (3R, 4R)-1 -carbo-(4-ethylbenzoxy)-3-ethyl-4[(1-methyl-1H-i idazol-5-yl)methyl]-2 -pyrrolidinone.

EXAMPLE 2

(3R,4R)-1-carbo-(4-trifluoromethylbenzoxy)-3-ethyl-4-[(1-methyl-1 H-imidazol-5-yl)methyl]-2-pyrrolidinone The title compound was prepared according to the procedure of Example 1, by substituting O-(4-nitrophenyl)-O'-(4-trifluoromethylbenzyl) carbonate for the carbonate of Example 1.

EXAMPLE 3

(3R,4R)-1-carbo-(2-methylthienylmethyloxy)-3-ethyl-4-[(1-methyl-1 H-imidazol-5-yl)methyl]-2-pyrrolidinone The title compound was prepared according to the procedure of Example 1, by substituting O-(4-nitrophenyl)-O'-(2-methylthienylmethyl) carbonate for the carbonate of Example 1.

EXAMPLE 4

(3R, 4R)-1-carbo-(2,4-dimethylbenzoxy)3-ethyl-4-[(1-methyl-1H-imidazol-5-yl)methyl]-2-pyrrolidinone The title compound was prepared according to the procedure of Example 1, by substituting O-(4-nitrophenyl)-O'-(2,4-dimethylbenzyl) carbonate for the carbonate of Example 1.

EXAMPLE 5

(3R, 4R)-1-carbo-(3-methylbenzoxy)3-ethyl-4-[(1-methyl-1 H-imidazol-5-yl)methyl]-2-pyrrolidinone The title compound was prepared according to the procedure of Example 1, by substituting O-(4-nitrophenyl)-O'-(3-methylbenzyl) carbonate for the carbonate of Example 1.

EXAMPLE 6

(3R, 4R)-1-carbo-(2,3-dimethylbenzoxy)3-ethyl-4-[(1-methyl-1 H-imidazol-5-yl)methyl]-2-pyrrolidinone The title compound was prepared according to the procedure of Example 1, by substituting O-(4-nitrophenyl)-O'-(2,3-dimethylbenzyl) carbonate for the carbonate of Example 1.

EXAMPLE 7

(3R, 4R)-1-carbo-(2-methylbenzoxy)3-ethyl-4-[(1-methyl-1 H-imidazol-5-yl)methyl]-2-pyrrolidinone The title compound was prepared according to the procedure of Example 1, by substituting O-(4-nitrophenyl)-O'-(2-methylbenzyl) carbonate for the carbonate of Example 1.

EXAMPLE 8

(3R, 4R)-1-carbo-(4-chlorobenzoxy)3-ethyl-4-[(1-methyl-1 H-imidazol-5-yl)methyl]-2-pyrrolidinone The title compound was prepared according to the procedure of Example 1, by substituting O-(4-nitrophenyl)-O'-(4-chlorobenzyl) carbonate for the carbonate of Example 1.

EXAMPLE 9

(3R,4R)-1-carbo-(1-naphthylmethyloxy)-3-ethyl-4-[(1-methyl-1H-imidazol-5-yl)methyl]-2-pyrrolidinone The title compound was prepared according to the procedure of Example 1, by substituting O-(4-nitrophenyl)-O'-(1-methylnaphthyl) carbonate for the carbonate of Example 1.

EXAMPLE 10

Test of Pharmacological Activity

Methods

The test compounds were topically applied in volumes of 25 ml (rabbits) or 10 ml (owl monkeys). Solutions with active ingredient concentrations ranging from 0.5% to 4% were tested. Pupil diameter was measured at times 0, 0.5, 1, 2, 3, 4, 5 and 6 hours after treatment. Normal saline was used as vehicle control, and pilocarpine (0.5–1%) as positive control. Intraocular pressure was also measured at the above times after treatment with selected compounds. Since most of the compounds were oil, they were initially dissolved in 0.01 N acetic acid and brought to the desired final volume with normal saline. The pH of all test solutions was adjusted by 5.

Results

Corneal penetration was determined by measuring miosis following topical application. Effect of the tested compounds of Formula (I) on pupil size in rabbits is shown in Table 1.

TABLE I

Activity of Isopilocarpine Lactam Compounds on Pupil Size in Pigmented Rabbits

| R | EXAMPLE | CONC (%) | Decrease in PUPIL DIAM[a] (mm.) | Time to MAX.[b] (hrs.) | Duration[c] (hrs.) |
|---|---|---|---|---|---|
| 1-napthylmethyloxy | 9 | 2 | 2.2 | 1 | 5 |
| 2-methyl-thienylmethyloxy | 3 | | | | |
| 4-trifluoro-methylbenzyloxy | 2 | 2 | 2.5 | 1 | 5 |
| 4-ethylbenzoxy | 1 | 2 | 2.3 | 1 | 4+ |
| 4-chlorobenzoxy | 8 | 1 | 1.3 | 1 | 6 |
| | | 2 | 1.7 | 1 | 6+ |
| 2-methylbenzoxy | 7 | 2 | 1.2 | 1 | 2 |
| 2,3-dimethylbenzoxy | 6 | 2 | 2.5 | 1 | 3 |
| 3-methylbenzoxy | 5 | 2 | 1.3 | 1 | 2+ |
| 2,4-dimethylbenzoxyl | 4 | 2 | 1.8 | 1 | 5+ |

Pupil diameter was measured at different times after topical application of the compounds.
[a] Maximum decrease in pupil diameter.
[b] Time the maximum effect was obtained.
[c] Time when there was at least 0.5 mm decrease in pupil diameter or maximum response was maintained.

Following topical application, miosis was caused by most of the compounds indicating improvement in corneal penetration. The extent of miosis ranged from about 3% to about 50% decrease in pupil size. The duration ranged from 1 hour to longer than 6 hours (duration of the experimental period). In general, duration was related to the extent of miosis. However, there were some compounds that caused little miosis which persisted through the experimental period. This suggested a depot effect.

EXAMPLE 11

Ophthalmic preparation

The composition of a typical ophthalmic preparation according to the invention is as shown herein below:

| Ingredient | Amount (% w/v) |
|---|---|
| Active ingredient | 0.15 |
| Benzalkonium Chloride | 0–0.10 |
| Polyvinyl Alcohol (Grade 20-90) | 0–40 |
| Sodium Chloride | 1–10 |
| Sodium Citrate, Dihydrate | 0.01–10 |
| Citric Acid, Monohydrate | 0.01–2 |
| Purified Water | q.s. to make 100% |

While particular embodiments of the invention have been described, it will be understood, of course, that the invention is not limited thereto since many obvious modifications can be made, and it is intended to include within this invention any such modification as will fall within the scope of the appended claims.

Having now described the invention, we claim:

1. A compound of Formula 1 including optical isomers and racemic mixtures of said isomers

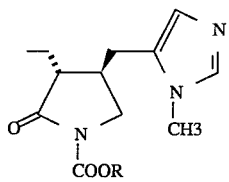

Formula 1 wherein R is

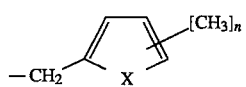

wherein n is 0 or an integer of 1 or 2 and X is O or S, and pharmaceutically-acceptable salts thereof.

2. A compound according to claim 1 wherein X is O.

3. A compound according to claim 1 wherein X is S.

4. A pharmaceutical composition containing a therapeutically effective amount of at least one compound defined in claim 1 as active ingredient, in admixture with a conventional pharmaceutical excipient.

5. A pharmaceutical composition according to claim 4 in the form of an ophthalmic solution.

* * * * *

UNITED STATES PATENT AND TRADEMARK OFFICE
CERTIFICATE OF CORRECTION

PATENT NO. : 5,453,434
DATED : September 26, 1995
INVENTOR(S) : Albaugh et al

It is certified that error appears in the above-indentified patent and that said Letters Patent is hereby corrected as shown below:

Title page, item [54], & Col. 1, line 4, "PYRROLIDONE" should read
--PYRROLIDINONE--

Col. 4, line 14, after "to" insert --,--

Signed and Sealed this

Twenty-third Day of January, 1996

Attest:

BRUCE LEHMAN

*Attesting Officer*   Commissioner of Patents and Trademarks